United States Patent [19]

Terino

[11] Patent Number: 4,790,849

[45] Date of Patent: Dec. 13, 1988

[54] MALAR IMPLANT AND METHOD OF INSERTING THE PROTHESIS

[76] Inventor: Edward Terino, 2660 Townsgate Rd., No. 740, Westlake Village, Calif. 91361

[21] Appl. No.: 4,819

[22] Filed: Jan. 5, 1987

Related U.S. Application Data

[63] Continuation-in-part of Ser. No. 769,194, Aug. 23, 1985, abandoned.

[51] Int. Cl.[4] .............................................. A61F 2/10
[52] U.S. Cl. ........................................ 623/11; 623/16
[58] Field of Search ................................. 623/11, 16; 128/DIG. 21

[56] References Cited

U.S. PATENT DOCUMENTS

| | | | |
|---|---|---|---|
| 3,720,959 | 3/1973 | Hahn | 623/16 |
| 3,849,805 | 11/1974 | Leake et al. | 128/92 Y |
| 4,344,191 | 8/1982 | Wagner | 128/92 C |

FOREIGN PATENT DOCUMENTS

| | | | |
|---|---|---|---|
| 2806207 | 8/1979 | Fed. Rep. of Germany | 623/16 |
| 2447182 | 9/1980 | France | 623/11 |

OTHER PUBLICATIONS

Lynch, "Implants, Reconstr. the Hum. Body", Van Nostrand Reinhold Co., N.Y. 1982, pp. 148–149.
Anastasov, "Method for Reconstr. of the Orbital Floor & Ant. Wall of the Maxillary Sinus", British Journal of Plastic Surgery, vol. 18, No. 2, 1965, pp. 204–207.
Hinds, "Proplast in Dental Facial Reconstruction", Oral Surgery, Oral Medicine, Oral Pathology, vol. 39, No. 3, pp. 347–355, Mar. 1975.

*Primary Examiner*—Richard J. Apley
*Assistant Examiner*—David J. Isabella
*Attorney, Agent, or Firm*—Richard D. Slehofer

[57] ABSTRACT

A malar implant molded from silastic material is surgically implanted behind the soft tissue of the cheek and over the malar zygomatic complex to buildup the prominence of the cheekbone. The implant has a convex front surface and a concave back surface for close fitting to the cheekbone. The front surface includes a prominence to replicate the prominence of a high cheekbone and the posterior end tapers off. This structure, after implantation appears natural and gives the appearance of attractive high cheekbones on the patient. The protheses come in left and right mirror image pairs for implantation on the left and right cheeks by practicing a new surgical procedure.

15 Claims, 2 Drawing Sheets

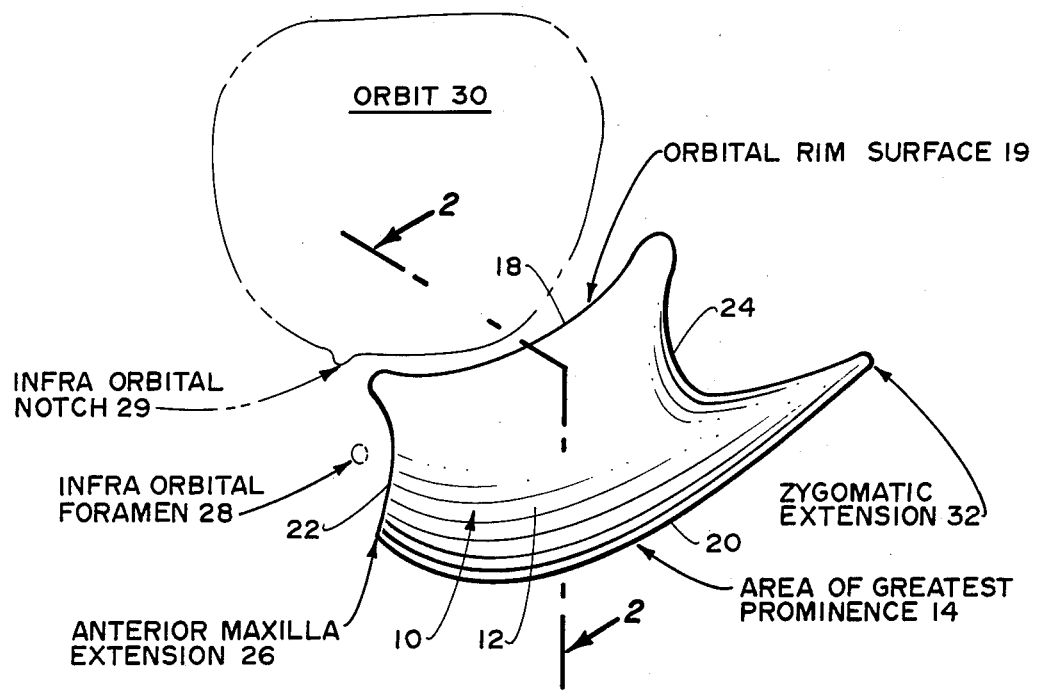
Fig. 1.
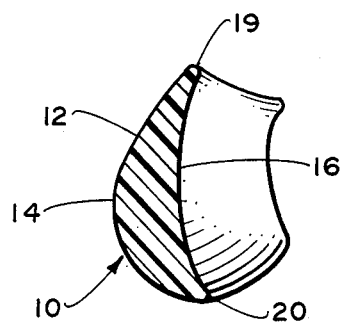
Fig. 2.
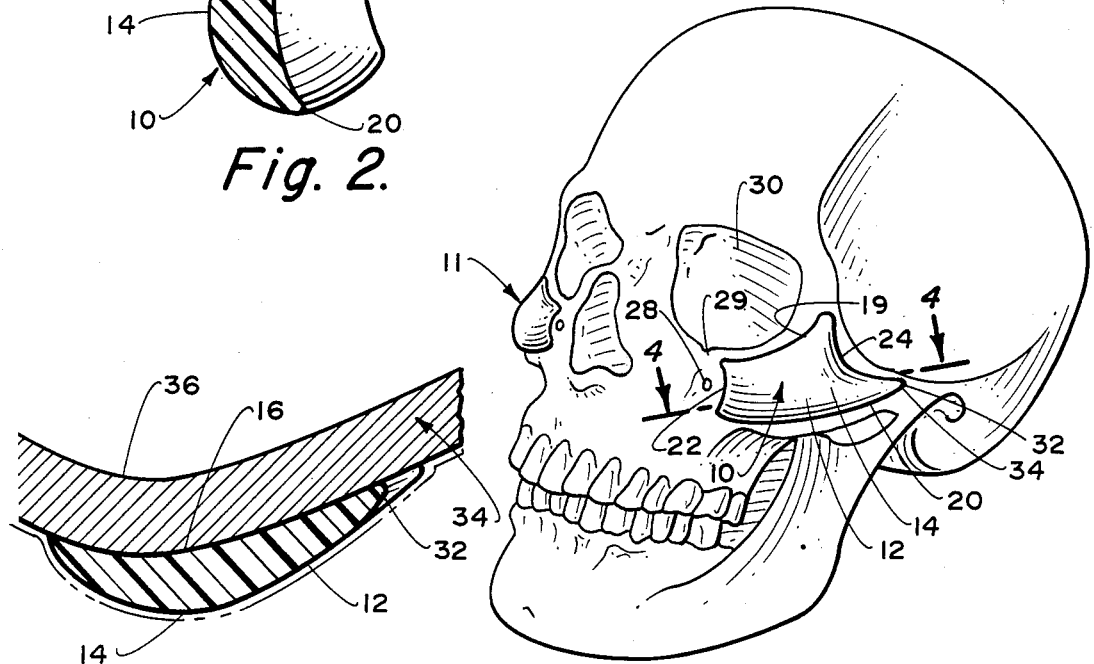
Fig. 4.
Fig. 3.

MALAR IMPLANT AND METHOD OF INSERTING THE PROTHESIS

This application is a continuation-in-part of application Ser. No. 769,194, filed Aug. 23, 1985, now abandoned.

BACKGROUND OF THE INVENTION

1. Field of the Invention

The present invention pertains to surgery. And more particularly to the orthopedics of reconstructive and aesthetic surgery including a bone prothesis and to a surgical method of implanting the prothesis on the malar, or cheek bone, of a patient.

2. Description of the Prior Art

The medical speciality of facial cosmetic surgery, reconstructive and plastic surgery involves reconstruction of the cutaneous tissues around the neck and face, which is performed to correct defects and to remove the marks of time.

It has also been developed to improve, or correct, the facial features of a patient. For example, Rhytidoplasty, or face lift, is performed to remove excess skin and tighten the remaining skin to give a more youthful appearance to an older person. Rhinoplasty has been developed to improve the shape and contour of the patient's proboscis. Blepharoplasty is performed to remove wrinkles and bulges around the eyelids.

Many deformities by birth, accident, infection, cancer removal, or surgical necessity may need reconstruction by implanting prothesis as well as reconstructing the bony facial skeleton.

Surgical implants have also been developed in conjunction with these surgical techniques to also alter the appearance of the chin and nose by implanting a prothesis. The chin implant is surgically inserted and positioned on the mandible to buildup the chin and give it a more pleasing appearance. This procedure is called Mentoplasty. An example of such an implant is disclosed in Wagner, U.S. Pat. No. 4,344,191.

The inventor of the present invention, who is a Plastic Surgeon, saw the continued need for new surgical implants and new plastic surgery procedures in an ongoing effort to improve the effectiveness of plastic surgery. As a result of this need, the inventor invented the malar implant and the surgical procedure for correctly implanting it on the patient.

SUMMARY OF THE INVENTION

An object of the present invention is to provide a malar implant positioned between the malar-zygomatic bone complex and the fleshy portion of the side of the face commonly referred to as the cheek for increasing the prominence of the cheek below the eye orbit of the patient. The prominent appearing cheek bones impart a more handsome or pleasing appearance to the facial features of a patient.

Another object of the present invention is to provide a malar or cheek implant which will raise the cheeks of an older patient to lessen the effects of aging thereby giving a patient a more youthful appearance after the implantation of the left and right pair of malar implants.

It is another object of this invention to provide for a surgical procedure for inserting the malar implant on the malar-zygomatic bone complex of the patient.

Another object is for restoration of the facial skeleton after traumatic injury, or accident, to the malar, zygomatic and chin regions.

The malar implant is intended for both reconstructive and cosmetic plastic surgery. It is positioned adjacent to the human eye socket and overlies the malar-zygomatic bone complex. The implant is comprised of a 3-dimensional asymmetrical implant which is molded or fashioned from an inert plastic material, or silicone sold under the trademark Silastic. The implant generally has an outer and inner surface. The outer surface has a distinct convex surface which forms the prominence of the cheek area after the implant is in place. The inner surface of the implant includes a concave depression, or recess. The complementary concave depression of the malar implant fits the overal contour and curves of the zygomatic bone in the area of the implant almost precisely. The posterior contour of the outer surface of the malar implant is shaped to mimic the normal anatomy of the facial skeleton.

The outer surface and the inner surface of the implant merge to form an upper edge, a lower edge, a leading or anterior edge and a trailing or posterior edge. The corner where the anterior edge and the upper edge merge is generally positioned below the infraorbital notch below the eye socket or orbit. The anterior edge is receded sufficiently to avoid and to provide space for the infraorbital foramen when in place on the patient. The upper edge forms an orbital rim surface below the orbital rim of the patient. The trailing or posterior edge can include a zygomatic extension for causing part of the zygomatic arch of the patient to appear more prominent after the implant is in place on the patient.

In another embodiment of the implant, the anterior edge includes a maxilla extension extending from the lower region of the anterior edge to enhance the anterior maxilla and lower orbit region when necessary or desirable.

In yet another embodiment, the aforementioned anterior maxilla extension includes a hook-shaped extension having a cut-away for avoiding and providing space for the infraorbital foramen and the infraorbital notch. The hook-shaped extension creates an orbital rim surface extension which is juxtaposed along the rim surface formed by the upper edge of the implant.

In still yet another embodiment of the invention, the modification is where the anterior edge and the lower edge converge to form a curvilinear edge from the anterior edge-lower edge juncture up to the anterior edge-upper edge juncture. The point where the anterior edge and the posterior edge meet is very rounded. The silhoutte of this embodiment resembles a four-pointed diamond shape having four sides with the bottom point almost indistinguishable; one lateral point is adjacent the zygomatic arch; the other lateral point is adjacent the infraorbital foramen; the top point is adjacent the orbit; and the bottom nearly muticous point lies adjacent the maxilla bone.

The malar implant can be fabricated by means of molding a solid, biologically inert, pliant, flexible and compressible material such as plastic, or a silicone rubber sold under the brand name Silastic. The implant could have of a jell-filled sac construction if desired. The malar implant could be fabricated as a rigid piece of plastic if desired. It may also be fashioned from other bio-implantable materials.

It is to be recognized and understood that under normal conditions there will be a pair of identical mirror image shaped implants implanted one in the left cheek and the other in the right cheek of the patient. The implant could be tailored somewhat to the individual patient to form a custom fit against the malar-zygomatic complex of the patient. However, the pliant and flexible nature of the implants should allow this complementary fitting without much customization required beforehand or during the surgical operation.

The malar implants can be offered in three sizes; small, medium and large to accomodate the normal range of patients' facial skeleton sizes. It can also be modified into other sizes if necessary.

There is a surgical operation or method of implanting the prothesis in the patient which includes the steps of making the appropriate incisions, creating a pocket for receiving the implant, inserting the implant with the appropriate tools and repairing the incision with routine closure techniques.

BRIEF DESCRIPTION OF THE DRAWINGS

FIG. 1 illustrates a perspective view of the first embodiment of the malar implant properly positioned below the patient's orbit with the anterior edge positioned slightly below the infraorbital notch and avoiding the infraorbital foramen.

FIG. 2 is a cross-sectional view taken along the line 2—2 of FIG. 1.

FIG. 3 is a perspective view of the facial skeleton showing the implant of FIG. 1 properly positioned on the malar-zygomatic bone complex.

FIG. 4 is a cross-sectional view taken along the line 4—4 of FIG. 3.

DETAILED DESCRIPTION OF THE EMBODIMENTS

Figure 5:
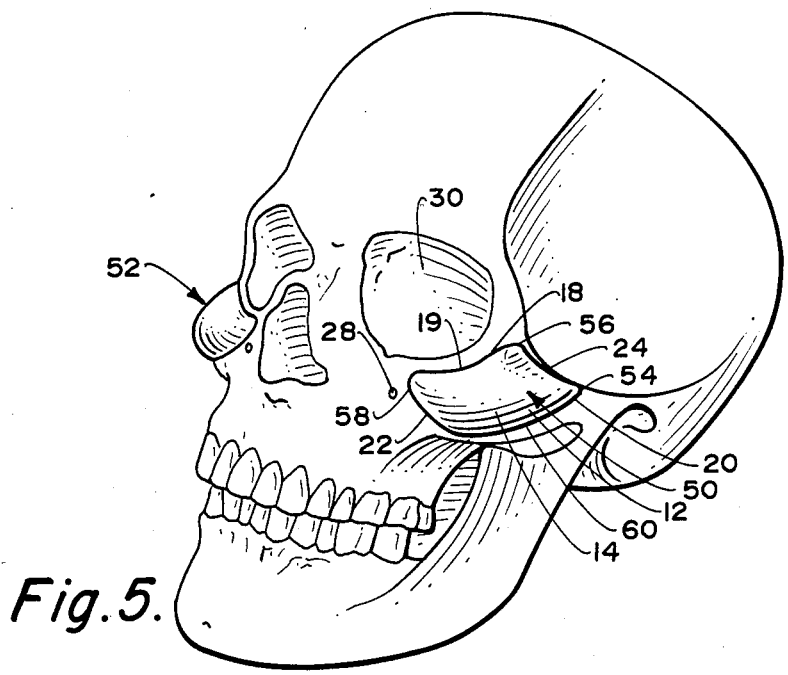
FIG. 5 illustrates a perspective view of the facial skeleton showing the left and right implants of a second embodiment of the implant properly positioned on the malar-zygomatic bone complex.

Referring now to FIG. 1, there is illustrated the first embodiment of the malar implant overlying the malar-zygomatic bone complex on the left side of the patient. It is generally labelled as No. 10. The implant 10 has a 3-dimensional asymmetrical configuration. There is an outer surface means 12 illustrated as a generally convex surface having an area of greatest prominence at the apex 14 at the lower mid-region of the outer surface 12. The outer face 12 forms a prominent appearing cheek bone when the implant 10 is implanted on the patient.

The inner surface means 16 is illustrated as a generally concave surface, or deep recess in the backside of the implant, which forms a complementary fit with the underlying cheekbone region of the patient. The cheekbone region includes the superior maxilla and zygoma bones which form the malar-zygomatic complex. The cheekbone is the prominence below the eye that is formed by the zygomatic bone. The malar bone is a four-pointed bone on each side of the face, uniting the frontal and superior maxillary bones with the zygomatic process of the maxilla.

FIG. 2 shows a cross-sectional view of the implant 10 of FIG. 1 taken along the lines 2—2 of FIG. 1. The greatest prominence of the outer face is clearly illustrated in FIG. 2 as the apex 14. The outer surface has an overall convex shape. A longitudinal cross-sectional view of the outer surface illustrates a convex surface. Transverse cross-sectional views of the outer surface illustrate a variable convex contour. The transverse contour is most acute at the area of greatest prominence, and becomes less acute on either side of 14. The concave inner surface also has a complementary area of greatest depression positioned underneath 14. The longitudinal cross-sectional view of the inner surface illustrates a generally concave contour. Transverse cross-sectional views of the inner surface disclose a variable concave contour. The concave contour of the transverse cross-section is most acute at the area of greatest depression, and becomes less acute on either side of the depression.

Referring back to FIG. 1, the outer surface 12 and the inner surface 16 merge at the superior portion of the implant to form the upper edge 18, and they merge at the inferior portion to form the lower edge 20. The outer and inner surfaces merge at the anterior portion to form the anterior edge 22, and they taper at the posterior portion to form the posterior edge 24.

The anterior edge 22 includes a maxilla extension 26 extending from the lower region where the anterior edge 22 and the lower edge 20 converge. The portion of the implant above this lower region is sufficiently receded, or indented, to avoid and to provide space for the infraorbital foramen 28 when the implant is correctly positioned on the patient.

The infraorbital foramen is an opening, or orifice, in the maxilla bone to provide a passageway for several vessels including the infraorbital nerves to the facial area of the cheek and upper lip. Physical contact with these nerves by the implant would result in discomfort and perhaps disabling symptoms in the immediate area and down into the upper lip and cheek area innervated by the infraorbital nerve.

Part of the upper edge 18 formed at the superior portion of the implant forms an orbital rim surface 19. This orbital rim surface is positioned below and generally parallels the lower edge of the orbit 30, or eye socket, of the facial skeleton. The distance between the orbit and the orbital rim surface 19 is about 4 millimeters.

The posterior edge 24 of the implant 10 includes a zygomatic extension means 32 where the lower edge 20 and the posterior edge 24 converge. The zygomatic extension means is illustrated as a tapered tail 32 extending from the posterior edge 24. The zygomatic extension 32 overlays part of the zygomatic arch 34.

FIG. 3 illustrates the human skull with the left malar implant 10 correctly positioned on the left side of the face over the malar zygomatic complex and below the orbit 30. It is positioned posterior to the infraorbital foramen 28. The anterior end of the orbital rim surface 19 is positioned below the infraorbital notch 29. The right malar implant 11 is likewise correctly positioned on the right side of the face. The left implant 10 and the right implant 11 are for the most part mirror images of each other and are positioned on the facial skeleton in a mirror image fashion. In practice, the two implants would be sold in pairs with an L and an R imprinted on the left and right implant respectively to avoid confusion by the attending surgeon. There would also be placed a dot on the superior portion to avoid the mistake of placing either of the implants upside down in the cheek.

FIG. 4 is a cross-sectional view of the implant 10 taken along the lines 4—4 of FIG. 3. This view illustrates the cross-section of the malar zygomatic complex 36 in cooperation with the inner concave surface 16 of the implant. The zygomatic extension 32 is positioned against the zygomatic arch 34. The posterior contour of the trailing edge of the zygomatic extension 32 of the implant 10 fits the contour of the skeleton in that area almost precisely. The posterior contour of the zygomatic extension 32 and the outer surface 12 are shaped to mimic the normal anatomy of the facial skeleton. As a result of this contouring, the implanted protheses give very natural appearing cheeks on both sides of the face.

FIG. 5 illustrates a mirror image pair of second embodiments 50 and 52 of the malar implant. It is fitted to the malar zygomatic complex in the same manner as the first embodiment 10 is fitted. The implant 50 has the same elements as the implant 10 has. It has a convex front surface 12 with an apex or area of greatest prominence 14, a back surface face 16 with an area of greatest depression, a lower edge 20, an upper edge 18, an anterior edge 22, and a posterior edge 24. The second embodiment has the same crosssections as are illustrated in FIGS. 2 & 4. The implant 50 has a silhoutte which resembles a four-pointed diamond shape having four sides in a very general sense. One lateral point 58 is adjacent the infraorbital foramen; the other lateral point 54 is adjacent the zygomatic arch; the top point 56 is adjacent the orbit; and the bottom point 60 is adjacent the maxilla bone. Beginning at the top point 56 and going in a clockwise direction, the first side is the posterior edge 24, the second side is the lower edge 20, the third side is the anterior edge 22, and the fourth side is the upper edge 18. The lower edge 20 and the anterior edge 22 meet to form a very rounded corner. The combination of the lower edge and the anterior edge appear to form a curvilinear edge because of the nearly indistinguishable corner.

Figure 6:
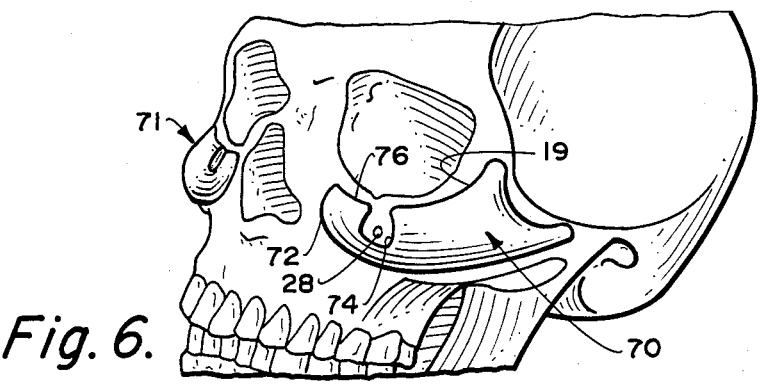
FIG. 6 is a perspective view of a third embodiment of a pair of implants properly positioned on the malar-zygomatic bone complex of the skull.

A third embodiment 70 of the malar implant is illustrated in FIG. 6. Its configuration is nearly identical to the implant 10 shown in FIG. 1 with the addition of a hook-shaped extension means 72 formed as part of the ancillary maxilla extension 26. The hook-shaped extension means is illustrated as a hook-shaped extension having a cutaway 74 for avoiding and providing space for the infraorbital foramen, and an infraorbital rim extension medially 76 juxtaposed with the orbital rim surface 19 for more definition of the cheek area anterior to the infraorbital foramen 72. The mirror image of the implant 70 is numbered 71.

Figure 7:
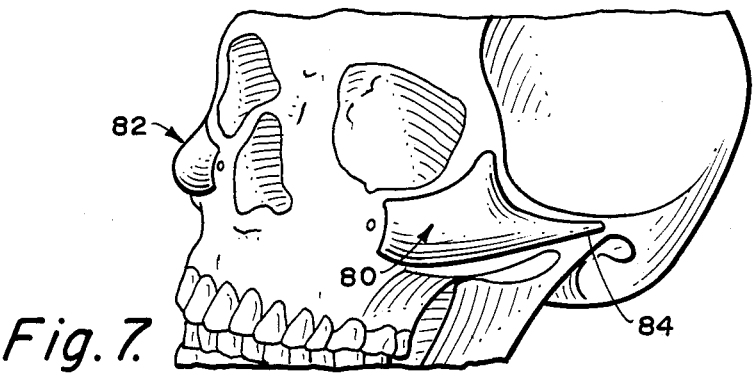
FIG. 7 is a perspective view of the left and right implants of a fourth emodiment of the malar implant properly positioned on the malar-zygomatic bone complex of the skull or facial skeleton.

A fourth embodiment of the malar implant is numbered 80, and is illustrated in FIG. 7. The configuration is nearly identical to the malar implant 10 which has already been described, and illustrated in FIGS. 1 through 3, with the additional feature of having the zygomatic extension labelled as 32 in FIG. 1 extending further backwards towards the ear. This feature 84 gives more definition to the zygoma. The mirror image of the implant 80 is numbered 82.

The four described malar implants should give the surgeon, using his skill and judgment, enough inventory to choose and fashion the appropriate implant to be used on a particular patient. Some patients have a more rounded face, some have a narrow gauntlike appearance, while others fall into the normal category.

Figure 8:
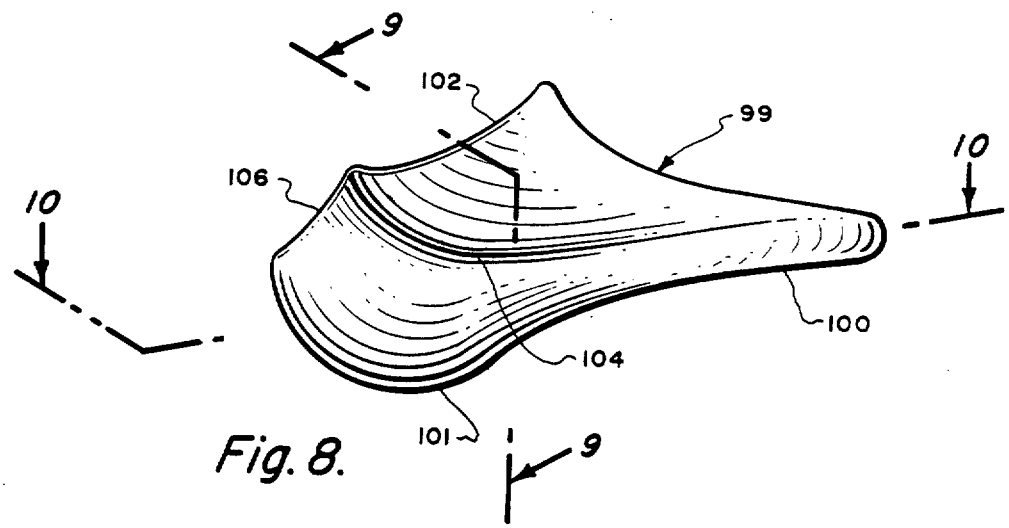
FIG. 8 illustrates a perspective view of an alternative embodiment of the Malar Implant having an inferior extension extending below the lower edge.
Figures 9, 10:
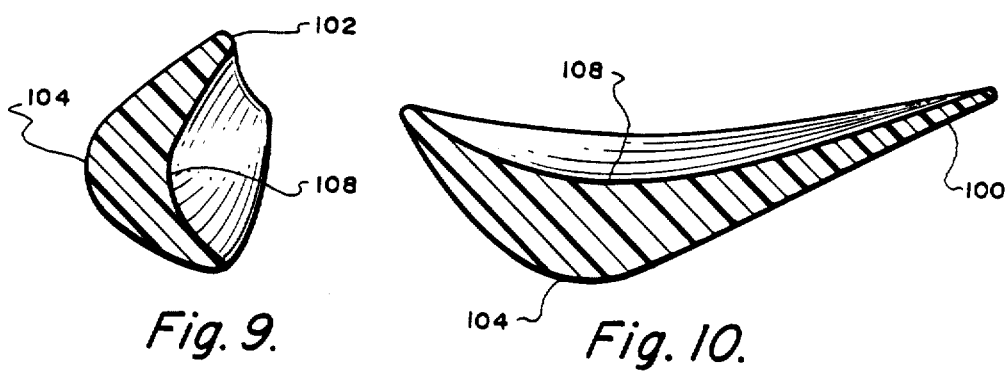
FIG. 9 is a transverse cross sectional view of the extended implant taken along the lines 9—9 of FIG. 8.
FIG. 10 is a longitudinal cross sectional view taken along the lines 10—10 of FIG. 8.
Figure 11:
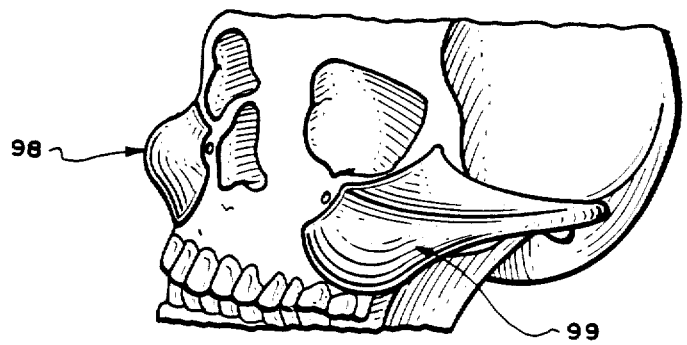
FIG. 11 is a fragmentary perspective view of the facial skeleton showing the implant in FIG. 8 properly positioned on the Malar - Zygomatic Bone complex.

Referring now to FIG. 8, there is illustrated an alternative embodiment of the Malar Implant, specifically the left sided one 99. This is an alternative style of the Malar Implant. The posterior extension 100 overlying the Zygoma has been modified to create a better imitation of Mother Nature and to give a better contour to the implant. The lower edge has been extended downwardly creating an inferior extension 101 of this style of the implant. This is done to mimmick Mother Nature and to create a pleasing aesthetic shape. In effect, the implant is changing Mother Nature. The upper two-thirds or so of this implant covers the bone and becomes fixed by encapsulation. The lower one-third or so would be about 0.1 to 2.5 centimeters and extends below the bone into the soft tissue. The implant then is maintained in place by the capsule formation around the silicon comprising the implant which essentially acts like a sling in the inferior aspect; holding it in position and in place as well as being held in place by the musculature on the skull on the one side and on the subtutaneous tissues on the other side. Maxilary extensions with holes for the infra orbital nerves are optional and can be designed into it. As the implant is lying on the zygomatic muscle group, the reconstruction of the image of the malar bone appears to be much large by 2 to 4 centimeters than is the actual case of the patient. The transverse cross sectional view of the implant (FIG. 9) taken in conjunction with the longitudinal cross sectional view of the implant, FIG. 10, indicates that there is an area of greatest prominence 104 on the outer surface. FIG. 8 illustrates the zygomatic extension 100, the orbital rim surface 102, the area of greatest prominence 104, the anterior maxila extension 106. The outer convex surface is shown in FIG. 8 and cross sections of the inner concave and outer convex surfaces are shown by cross sectional views in FIGS. 9 and 10. The outer convex surface in the lower mid-region thereof has a convex surface in both a longitudinal and transverse cross section such that at an intersection 104 of the surface forms a maximum apex to yield an area of greatest prominence for forming a naturally appearing cheekbone when implanted. The inner concave surface in the lower mid-region thereof has a concave surface in both a longitudinal and transverse cross-section such that at the intersection 108 of the inner concave surface forms a maximum depression to provide a complementary fit adjacent to the underlying zygomatic bone.

Figure 12:
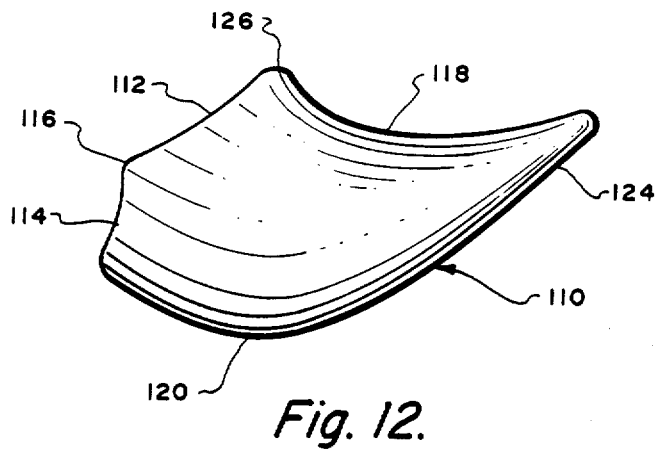
FIG. 12 illustrates a perspective view of another embodiment of the Malar Implant.

FIG. 12 shows another style of the Malar Implant generally designated as 110. The discussions regarding the implant shown in FIGS. 1 through 7 apply to this implant also. The modifications are where the upper edge 112 meets the anterior edge 114 at a point labeled No. 116. This point 116 is rounded off and tapered more so that the anterior edge 114 is slanted away from the infraorbital foramen. Additionally the posterior edge 118 meets with the upper edge 112 forming another modified point 126 which is not as prominent as that shown in FIG. 1. Additionally, where the lower edge 120 and the posterior edge 118 merge there is not as much of a extended zygomatic extension 124 as is shown in FIG. 1. The implant of FIG. 12 has the tips more rounded and a less prominent zygomatic extension. Again, the implant shown in FIG. 12 can be produced in generally three sizes, small, medium and large, to cover the anticipated range of patient's cheekbones. The concave surface of the implants generally have the area of greatest recess or depression to be placed against the zygomatic arch or cheekbone to keep it in position. It must be kept in mind, however, that due to injury or disease, occasionally the patient's cheekbone is not prominent enough and accordingly the concave area has to be modified somewhat and custom fitted so that it complements the surface as actually found in a particular patient. The end result is as before, because the convex outer surface is the one that creates the prominent appearing cheekbone. The concave surface will compensate for the abnormalities occasionally found in the patient.

METHOD OF INSERTING THE PROTHESES

The terms prothesis and implant are used interchangeably to denote the implants described herein, although it is to be understood that the method, or surgical procedure to be described, would cover any type of chin implant, not just those described herein. The surgical procedure includes the following steps:

1. Local or general anesthesia by surgeon's choice - normal anesthesia routine used in blepharoplasty or rhytidectomy procedures is recommended;
2. making a lower infratarsal blepharoplasty incision;
3. elevating a skin-orbicularis muscle flap;
4. using a fixation forcep to separate the orbital septum and its fat contents from the lower eyelid;
5. creating a subperiosteal space, or pocket, to extend from the lateralorbital rim to expand laterally, outward and down on the facial skeleton both toward the zygoma and down underneath the infraorbital foramen;
6. undermining if necessary around the lateral orbital rim.

The implant is properly positioned when the anterior tip of the orbital rim 19 is below the infraorbital notch 29, and the implant is posterior to the infraorbital foramen 28.

The lower edge 20 on the inferior extension 101 of the implant of FIG. 8 would extend and embed itself into that soft tissue that one can grab and which is termed by the layman as the cheek. The cheek includes several muscles and fatty tissues. The two face muscles known as Zygomaticus major and Zygomaticus minor originate or attach to the Zygomatic arch and behind the maxillary arch, respectively. The attachments of the muscles to the bones are called elevators. The two muscles referred to are the upper muscles of the upper lip, one of which draws the upper lip backwards, and the other one draws the upper lip up and out.

The Terino implants are held in place by the lower edge 20 on the inferior extension 101 which when implanted will cause the body to react to this foreign object by encapsulating the lower edge of the implant by forming a type of collagen fibrosis which will not stick to the implant but will snugly hold the lower edge 20 on extension 101 in place by forming a pocket to keep the implant from drifting downwards. The inner surface lying adjacent to the bone arch also serves to keep the implant from drifting.

The malar implant acts as a spacer to build up the insufficient prominence of the cheekbone. The outer face 12 of the implant is a replica of what the cheekbone would look like if the patient had a prominent cheekbone. The implant is intended to mimic the natural contours of a prominent cheekbone. The implant is positioned under the soft tissue of the cheek, and after healing, will give the patient the appearance of attractive high cheekbones.

Obviously, many modifications and variations are possible in light of the above teachings. It is therefore to be understood that the full scope of the invention is not limited to the details disclosed herein and may be practiced otherwise than as specifically described.

What is claimed is:

1. A malar implant used in cosmetic and reconstructive surgery for surgical incision adjacent the human eye socket and between the malar-zygomatic bone complex and the fleshy portion of the cheek area which comprises:

a three-dimensional asymmetrical implant having an outer generally overall convex surface having a lower region and a lower mid-region, and an inner concave surface;

said outer convex surface in said lower mid-region thereof, having a convex surface in both a longitudinal and transverse cross section such that at an intersection of the surfaces forms a maximum apex to yield an area of greatest prominence for forming a naturally appearing high cheekbone when implanted for aesthetic purposes and also for minimizing the sagging skin of the cheeks caused by the aging process;

said outer convex surface and said inner concave surface merging to form an upper edge, a lower edge, an anterior edge, and a posterior edge;

said anterior edge includes a maxilla extension extending from said lower region of said anterior edge;

said upper edge includes an upwardly extending orbital rim surface;

after said implant is implanted, said upper edge and said anterior edge, add support to the patient's lower eyelid to help the eyelid from descending with age to minimize the lower eyelid drooping caused by the aging process;

said posterior edge being arcuate shaped below the rearward end of said orbital rim surface and converging with said lower edge forming a rearwardly extending zygomatic extension.

2. The implant as recited in claim 1 wherein said lower edge includes an inferior extension which descends into the soft tissue of the cheek and causes the body to react to said implant by encapsulating said inferior extension by forming a type of collagen fibrosis which will not stick to said implant, but will snugly hold said inferior extension in place by forming a pocket to keep said implant from drifting downwards.

3. The implant as recited in claim 1 wherein said malar implant is pliant, flexible and compressible.

4. The implant as recited in claim 1 wherein said malar implant is comprised of a plastic selected from the group consisting of, silicone, silicon rubber, Silastic, or other acceptable bio-implantable material.

5. The implant as recited in claim 1 wherein said malar implant is comprised of a rigid plastic material.

6. The implant as recited in claim 1 further comprising a mirror image shaped implant for placement on the other cheek of the patient.

7. A method of placing a silicon rubber malar implant in a patient having a normal malar region comprising the following steps:
- making a transverse lower infratarsal blepharoplasty incision;
- elevating a skin-orbiaris muscle flap;
- using a fixation forcep to separate the orbital septum and its fat contents from the lower eyelid;
- creating a subperiosteal space or pocket to extend from the lateralorbital rim to expand laterally, outward and down on the facial skeleton both toward the zygoma and down underneath the infraorbital foramen;
- undermining if necessary around the lateral orbital rim;
- forming a pocket large enough for visualizing the implants symmetrically in place;
- inserting the implant having a posterior edge forming a rearwardly extending zygomatic extension with a smooth, broad forcep;
- feeding the lateral or zygomatic end in first; and
- pushing the implant downwards and medially underneath the infraorbital foramen area; and
- repairing the incision with routine closure techniques.

8. The method as recited in claim 7 further comprising:
- making an intraoral-buccal incision after making said lower infratarsal blepharoplasty.

9. The surgical method as recited in claim 7 further comprising the steps of:
- implanting a mirror image shaped implant on the opposite cheek of the patient in a generally mirror image fashion as that used in the placement of said first implant.

10. A malar implant used in cosmetic and reconstructive surgery for surgical incision adjacent the human eye socket and between the malar-zygomatic bone complex and the fleshy portion of the cheek area which comprises:
- a three-dimensional asymmetrical implant having an outer convex surface and an inner concave surface;
- the longitudinal cross-section of said outer surface being a convex contour;
- the transverse cross-section of said outer surface being a variable convex contour;
- said outer surface having an area of greatest prominence at the lower mid-region of said convex outer surface for forming a naturally appearing prominent cheekbone;
- said transverse cross-section having the most acute convex contour at said area of greatest prominence, said convex contour becoming less acute on either side of said area of greatest prominence;
- the longitudinal cross-section of said inner surface being a concave contour for close positioning of the implant against the malar-zygomatic complex;
- the transverse cross-section of said inner surface being a variable concave contour;
- said inner surface having an area of greatest depression at the lower mid-region of said concave inner surface for providing a snug fit against the underlying cheekbone;
- said transverse concave cross-section having the most acute concave contour at said area of greatest depression, said transverse concave contour becoming less acute on either side of said area of greatest depression;
- said inner and outer surfaces merging to form an upper edge, a lower edge, an anterior edge, and a posterior edge;
- said anterioer edge includes an arcuate shaped maxilla extension extending from the lower region of said anterior edge;
- said upper edge includes a diagonally extending orbital rim surface;
- said posterior edge being arcuate shaped below the end of said orbital rim surface and converging with said lower edge forming a rearwardly extending zygomatic extension.

11. The malar implant as recited in claim 1 wherein said zygomatic extension of said implant is prominent and elongated to lift the soft tissue overlying the zygomatic arch area thereby causing the zygomatic arch area to appear more prominent.

12. The implant as recited in claim 10 further comprising a hook-shaped extension extending from said anterior maxilla extension, said extension forming a slot with said anterior edge for providing a space for the infraorbital foramen and infraorbital notch, said hook-shaped extension forming an orbital rim surface extension medially juxtaposed with said upper edge of said implant.

13. A malar implant used in cosmetic and reconstructive surgery for surgical incision adjacent the human eye socket and between the malar-zygomatic bone complex and the fleshy portion of the cheek area which comprises:
- a three-dimensional structure resembling a four-pointed diamond shape in silhoutte having four sides, an outer convex surface, and an inner concave surface;
- the longitudinal cross-section of said outer surface being a convex contour;
- the transverse cross-section of said outer surface being a variable convex contour;
- said outer surface having an area of greatest prominence at the lower mid-region of said convex outer surface for forming a naturally appearing prominent cheekbone;
- said transverse cross-section having the most acute convex contour at said area of greatest prominence, said convex contour becoming less acute on either side of said area of greatest prominence;
- the longitudinal cross-section of said inner surface being a concave contour for close positioning of the implant against the malar-zygomatic complex;
- the transverse cross-section of said inner surface being a variable concave contour;
- said inner surface having an area of greatest depression at the lower mid-region of said concave inner surface for providing a snug fit against the underlying cheekbone;
- said transverse concave cross-section having the most acute concave contour at said area of greatest depression, said transverse concave contour becoming less acute on either side of said area of greatest depression;
- said inner and outer surfaces merging to form an upper edge, a lower edge, an anterior edge, and a posterior edge;
- said posterior edge and lower edge converge to form a first lateral point which is positioned against the zygomatic arch when the implant is in place;

said upper edge and said posterior edge converging to form a top point which is positioned adjacent the orbit when the implant is in place;

said upper edge and said anterior edge converging to form a second lateral point which is adjacent the infraorbital foramen when the implant is in place;

said anterior edge and said lower edge converging to form a bottom point which is positioned against the maxilla bone when the implant is in place.

14. The implant as recited in claim 13 wherein said bottom point is a very rounded corner, said lower edge and said anterior edge appearing to form a single curvilinear edge.

15. A malar implant used in cosmetic and reconstructive surgery for surgical incision adjacent the human eye socket and between the malar-zygomatic bone complex and the fleshy portion of the cheek area which comprises:

a three-dimensional structure resembling a four-pointed diamond shape in silhouette having four sides, an outer generally overall convex surface having a lower region and a lower mid-region, and an inner concave surface;

said outer convex surface in said lower mid-region thereof, having a convex surface in both a longitudinal and transverse cross section such that at an intersection of the surfaces forms a maximum apex to yield an area of greatest prominence for forming a naturally appearing high cheekbone when implanted for aesthetic purposes and also for minimizing the sagging skin of the cheeks caused by the aging process;

said inner and outer surfaces merging to form an upper edge, a lower edge, an anterior edge, and a posterior edge;

said posterior edge and lower edge converge to form a first lateral point which is positioned against the zygomatic arch when the implant is in place;

said upper edge and said posterior edge converging to form a top point which is positioned adjacent the orbit when the implant is in place;

said upper edge and said anterior edge converging to form a second lateral point which is adjacent the infraorbital foramen when the implant is in place;

after said implant is implanted, said upper edge and said anterior edge, add support to the patient's lower eyelid to help the eyelid from descending with age to minimize the lower eyelid from drooping caused by the aging process.

said anterior edge and said lower edge converging to form a bottom point which is positioned against the maxilla bone when the implant is in place.

* * * * *

UNITED STATES PATENT AND TRADEMARK OFFICE
CERTIFICATE OF CORRECTION

PATENT NO. : 4,790,849

DATED : December 13, 1988

INVENTOR(S) : Edward Terino

It is certified that error appears in the above-identified patent and that said Letters Patent is hereby corrected as shown below:

FIGURES 8 through 12, should appear as shown on the attached sheets.

On the Title Page, "2 Drawing Sheets" should read -- 4 Drawing Sheets --.

In the heading on the two sheets of drawing, "Sheet 1 of 2" should read -- Sheet 1 of 4 --; "Sheet 2 of 2" should read -- Sheet 2 of 4 --.

Column 7, line 28, "chain implant" should read -- molar implant --.

Signed and Sealed this

Fifteenth Day of August, 1989

*Attest:*

DONALD J. QUIGG

*Attesting Officer*  *Commissioner of Patents and Trademarks*